US008759572B2

(12) United States Patent
Viscardi et al.

(10) Patent No.: US 8,759,572 B2
(45) Date of Patent: Jun. 24, 2014

(54) PROCESS FOR THE PREPARATION OF THYROID HORMONES AND SALTS THEREOF

(75) Inventors: Carlo Felice Viscardi, Milan (IT); Enrico Cappelletti, Seregno (IT); Laura Galimberti, Fara Gera d'Adda (IT); Sonia Gazzetto, Cascientte d'Ivrea (IT); Loredana Sini, Orgosolo (IT)

(73) Assignee: Bracco Imaging S.p.A., Milan (IT)

( * ) Notice: Subject to any disclaimer, the term of this patent is extended or adjusted under 35 U.S.C. 154(b) by 19 days.

(21) Appl. No.: 13/515,712

(22) PCT Filed: Dec. 17, 2010

(86) PCT No.: PCT/EP2010/070118
§ 371 (c)(1),
(2), (4) Date: Jun. 13, 2012

(87) PCT Pub. No.: WO2011/073409
PCT Pub. Date: Jun. 23, 2011

(65) Prior Publication Data
US 2012/0296113 A1    Nov. 22, 2012

(30) Foreign Application Priority Data
Dec. 18, 2009   (EP) .................................... 09179805

(51) Int. Cl.
*C07C 229/36*   (2006.01)
(52) U.S. Cl.
USPC ......................................................... 562/447
(58) Field of Classification Search
CPC ............................ C07C 227/16; C07C 227/42
See application file for complete search history.

(56) References Cited

U.S. PATENT DOCUMENTS

| | | | |
|---|---|---|---|
| 2,889,363 A | 6/1959 | Ginger et al. | |
| 2,889,364 A | 6/1959 | Anthony et al. | |
| 2,993,928 A * | 7/1961 | Razdan et al. | 562/447 |

FOREIGN PATENT DOCUMENTS

| | | |
|---|---|---|
| IT | MI981997 A1 | 3/2000 |
| JP | S62-153237 A | 7/1987 |
| WO | 96-11904 A1 | 4/1996 |
| WO | 2009/136249 A1 | 11/2009 |

OTHER PUBLICATIONS

PCT International Search Report for PCT/EP2010/070118, mail date Apr. 4, 2011.
PCT Written Opinion of the International Searching Authority, mail date Apr. 4, 2011.
Clayton, J.C. et al, "The synthesis of thyroxine and related substances. Part VI. The preparation of some derivatives of DL-thyroxine", Journal of the Chemical Society, Perkin Transactions 2, Chemical Society, Letchworth, GB, Jan. 1, 1950, pp. 840-843, XP002545458, ISSN: 1472-779X.
Chalmers, J.R. et al., "The Synthesis of Thyroxine and Related Substances. Part V. A Synthesis of L-Thyroxine from L-Tyrosine", Jan. 1, 1949, http://pubs.rsc.org/doi:10.1039/JR9490003424, pp. 3424-3433.
Taylor, Jay E. et al., The Ohio Journal of Science, vol. 53(1), 1953, pp. 37-41.
First Office Action for New Zealand application No. 600908, mail date Mar. 15, 2013.
First Office Action for Australian application No. 2010332798, mail date May 14, 2013.
Office Action for Canadian application No. 2,784,544, mail date Oct. 3, 2013.
Office Action for Chinese application No. 201080057949.5, mail date Nov. 11, 2013 (English translation).
Office Action for Japanese application No. 2012-543799, mail date Dec. 10, 2013 (English translation).

* cited by examiner

*Primary Examiner* — Paul A Zucker
(74) *Attorney, Agent, or Firm* — M. Caragh Noone

(57) ABSTRACT

The present invention generally refers to a process for the preparation of L-thyroxine derivatives. More in particular, the present invention relates to a iodination reaction of an aromatic derivative with an appropriate iodinating agent, so to afford the related iodinated compound as disodium salt, which may represent a useful intermediate for the synthesis of the L-thyroxine mono-sodium salt, and the free form thereof.

16 Claims, 3 Drawing Sheets

PROCESS FOR THE PREPARATION OF THYROID HORMONES AND SALTS THEREOF

CROSS-REFERENCE TO RELATED APPLICATIONS

This application is the national stage application of corresponding international application number PCT/EP2010/070118 filed Dec. 17, 2010, which claims priority to and the benefit of European application no. EP09179805.8, filed Dec. 18, 2009, all of which are hereby incorporated by reference in their entirety.

The present invention relates to a process for the preparation of thyroid hormones derivatives comprising the iodination reaction of an aromatic substrate with an appropriate iodinating agent, so to afford the related iodinated compound and salts thereof.

BACKGROUND

Hormonal derivatives are a class of compounds which plays an important biological role in several essential metabolic transformations. Among said class, thyroid hormones, and particularly, iodinated biphenyl compounds such as, for example, thyroxine ((2S)-2-amine-3-[4-(4-hydroxy-3,5-diiodoxyphenossyl)-3,5-diiodophenyl]propanoic acid), often abbreviated as T4), and triiodothyronine (T3), represent important key molecules, being involved in controlling the rate of various metabolic processes in the body. In particular, the mono-sodium salt of both L-thyroxine and L-triiodothyronine are widely employed in the treatment of several pathologies related to the malfunctioning of thyroid.

A variety of processes for the preparation of T4 and T3 have been disclosed in the past, initially by using animal natural sources as starting material (see U.S. Pat. No. 2,889,363), and later on by enzymatic or bio-mimetic synthesis (see U.S. Pat. No. 2,889,364). A further enhancement has been described in WO 96/11904 (Baxter), where an organometallic oxidative coupling is performed in order to obtain the thyroxine hydrochloride derivative, subsequently converted in the corresponding sodium salt, as appropriate.

IT 1302201 (Bracco) disclosed a process for the synthesis of the mono sodium salt of the L-thyroxine with an improved overall yield compared to a similar process known in the art (see e.g. Chalmers et al., J. Chem. Soc. 1949, 3424). According to the prior art teaching, the preparation of the monosodium salt of L-thyroxine occurs, in the most of the cases, by a proper and controlled acidification of the corresponding disodium salt, substantially as per scheme I, which is identified as FIG. 1.

Typically, the reaction may be carried out by reacting the disodium salt with a strong inorganic acid, for instance hydrochloric acid, followed by a proper pH regulation by using an alkaline base, such as $Na_2CO_3$.

Figure 2:
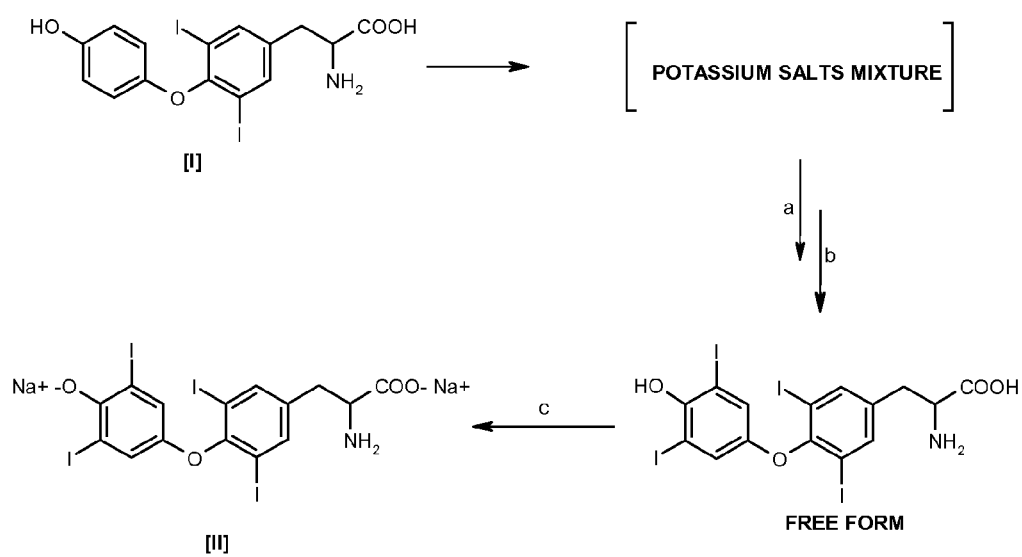

In its turn, the disodium salt formerly indicated as compound II may be prepared, for instance, as disclosed in IT 1302201 (Bracco), according to the Scheme II, which is identified as FIG. 2.

As schematically shown above, the 3,5 diiodo thyronine (compound I) is reacted with the widely used $KI/I_2$ system as the iodinating agent of choice (see for instance Taylor et al. The Ohio Journal of Science, Vol. 53, 37-41, 1953), in an aqueous medium and in the presence of a suitable amine.

The so obtained mixture of mono and di-potassium salts (herein general referred as "potassium salt mixture") is subjected to a subsequent separation and purification steps, including:
(a) the addition of an organic acid;
(b) the separation of the thus obtained "free form" (as a precipitate); and
(c) the final addition of an excess of sodium hydroxide to obtain the L-thyroxine di-sodium salt of formula II.

The applicant has now found a new process whereby compound II can be directly obtained by a conversion of compound I, substantially avoiding the above mentioned supplementary steps (a-c).

In particular, we have now found that by using $NaI/I_2$ in lieu of $KI/I_2$ as iodinating system, the iodination of the 3,5-diiodo thyronine of formula I leads to the L-thyroxine di-sodium salt II, in one step and in high yields and degree of purity. Surprisingly, in fact, and different to the corresponding potassium salt derivative of the prior art, the thus compound II is substantially insoluble in the reaction medium, and it may be promptly collected as such, or even employed as intermediate either in the preparation of the corresponding mono sodium salt or in the preparation of the free form thereof, as described below.

SUMMARY OF THE INVENTION

The present invention relates to a new process for the preparation of the sodium salts of the thyroidal hormone derivative thyroxine (T4), and free form thereof, by directly iodinating the 3,5-diiodo-thyronine of formula I in the presence of NaI and $I_2$.

In particular, the present invention relates to a process for the preparation of a thyroid hormone derivative, comprising reacting the compound of formula I:

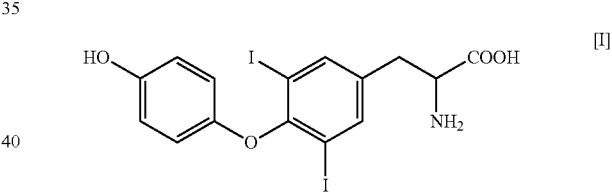

with an iodinating agent comprising NaI and $I_2$, in the presence of an aliphatic amine, to obtain the disodium derivative of formula II

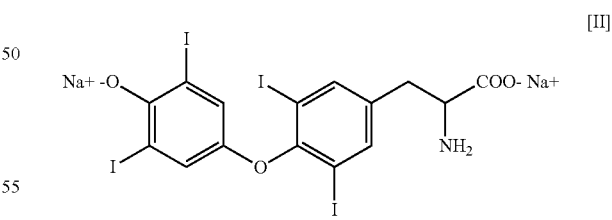

Preferably, the molar ratio between NaI and $I_2$ in the iodinating agent of choice is from 1 to 4, more preferably, from 2 to 3, whereas the aliphatic amine is preferably selected from linear mono ($C_1$-$C_4$) amines, being ethylamine the most preferred one.

The addition of the iodinating agent is carried out in the presence of an aqueous solvent, preferably in the presence of water, at a temperature preferably not higher than 25° C., more preferably at a temperature not higher than 22° C., for about 3-4 hours.

Once the iodination reaction is completed, a precipitate comprising the disodium salt II as a crude, is obtained. The final pH is preferably adjusted to basic values of at least 11, preferably by using an inorganic base, and the obtained L-thyroxine disodium salt II as pure compound is then collected, preferably by precipitation from an hydroalcoholic solution. Preferably said solution is a mixture of water/lower ($C_1$-$C_4$) alcohol at a temperature, and the precipitation is carried out by heating the solution at a temperature of about 50-70° C. followed by cooling at a temperature of about 5-15° C. The thus obtained L-thyroxine disodium salt in pure form may be either stored as such or used as intermediate in the preparation of the corresponding mono-sodium salt of formula III or in the preparation of the corresponding free form thereof of formula IV.

Therefore, and according to a further aspect of the invention, the L-thyroxine disodium salt II, is used in the preparation of the corresponding L-thyroxine mono-sodium salt of formula III.

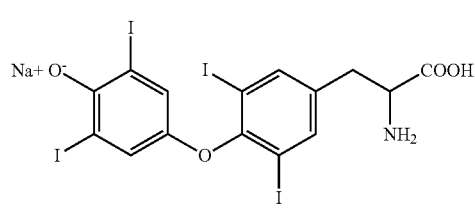

[III]

According to a preferred embodiment of the invention, the present process allows the preparation of compound III by means of a basification/acidification step of an aqueous solution of the di-sodium derivative II, being the latter prepared according to the present invention, so to obtain a pH ranging from 9 to 11. Preferably, such step is carried out by adding an organic weak acid to an alkaline aqueous solution of the disodium derivative II, at a temperature of at least 70° C. Preferably, the process temperature in the formation of the mono-sodium derivative of formula III is comprised from about 70° C. to about 95° C., still more preferably from about 75° C. to about 85° C.

A preferred organic acid is acetic acid, whereas preferred alkaline solution is a solution of compound II in distilled water, in the presence of $Na_2CO_3$ or NaOH. According to a further preferred embodiment, the water content of the alkaline solution of the compound II is comprised from about 11 to about 25 w/w, more preferably from about 11 to about 15 w/w.

In a similar way, and according to a further aspect, the present invention refers to a process for the preparation of the free form of the L-Thyroxine of formula IV

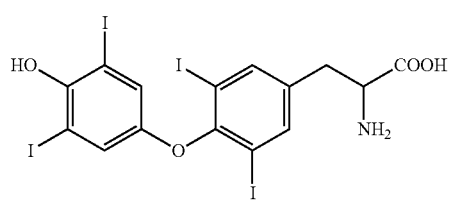

[IV]

by means of a basification/acidification step of an aqueous solution of the disodium salt II, being the latter prepared according to the present invention, so to obtain a pH lower than 8, preferably lower than 6.

DETAILED DESCRIPTION OF THE INVENTION

The present invention relates to a process for the preparation of a thyroid hormone derivative comprising reacting the compound of formula I,

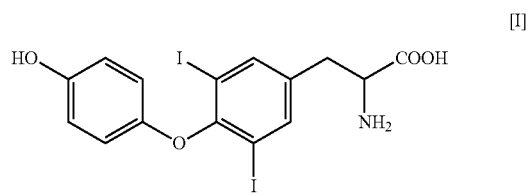 [SMILES: NC(Cc1cc(I)c(Oc2ccc(O)cc2)c(I)c1)C(=O)O]

[I]

with a iodinating agent comprising, or preferably consisting in NaI and $I_2$, in the presence of an aliphatic amine, to obtain the disodium derivative of formula II

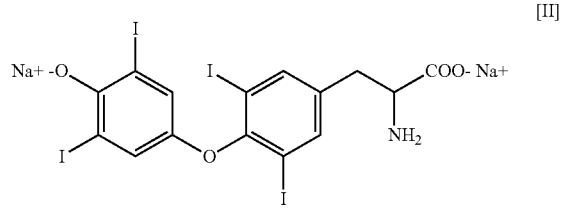

[II]

The iodinating agent of the present invention is preferably prepared by dissolving NaI and $I_2$ in an aqueous medium, preferably in water, more preferably in distilled water. Such aqueous solution hereinafter referred to as the "NaI/$I_2$ system", may be advantageously prepared either at the moment of use (i.e. just before the iodination reaction), or beforehand (e.g. from few to several hours before) and kept at room temperature before its use. According to an embodiment of the invention, the molar ratio between NaI and $I_2$ in the iodinating agent is from 2 to 3, preferably from 2.40 to 2.70.

In a practical preferred embodiment, the 3,5-diiodo thyronine of formula I is suspended in an aqueous medium, preferably water, even more preferably distilled water, in the presence of a proper organic amine.

Preferred amines are, for instance, aliphatic ($C_1$-$C_4$) amines, in particular linear mono ($C_1$-$C_4$) amines including, inter alia methylamine, ethylamine, propylamine and mixtures thereof, being ethylamine more preferred. The NaI/$I_2$ system is subsequently added thereto over about 2 to 5 hours, at a temperature equal or lower than 25° C., preferably not higher than 22° C. Preferably, the molar ration of the NaI/$I_2$ system with respect to the compound of formula I is of at least 1:2, even more preferably the molar ratio is comprised from 1:2 to 1:4.

Once the addition is completed, the reaction mixture is allowed to react at room temperature (i.e. from about 20° C. to about 35° C.), from at least one hour, and once the reaction is completed, the excess of amine is distilled off, for instance under reduced pressure, and a weak organic acid (which means an acid having a logarithmic acid dissociation constant pKa higher than −2), preferably acetic acid, is added at a temperature from about 10° C. to about 20° C., thus obtaining a precipitate containing the L-thyroxine disodium salt of formula II as a crude. According to a preferred embodiment, the thus obtained crude product is further purified by precipitation, by dissolving it in an hydroalcoholic solution, preferably in a mixture of distilled water/lower ($C_1$-$C_4$) alcohol, even more preferably in a mixture of distilled water/ethanol, by heating said solution to a temperature from 40° C. to 80° C., followed by cooling the heated solution at a temperature from about 5° C. to about 20° C., for example by means of an ice/water bath. Preferably, the weight ratio of water to alcohol in the hydroalcoholic mixture is 1:9, even more preferably 1:7. Before heating the solution, the pH is adjusted to basic values, preferably higher than 11, by addition of a base. Among the bases which can be used in this respect, an aqueous solution of the commonly inorganic bases such as alkaline metal hydroxides, carbonates, and the like may be conveniently employed, whereas aqueous NaOH is preferred, and aqueous $Na_2CO_3$ is even more preferred.

The L-thyroxine disodium salt II is thus collected as precipitate, e.g. by filtration, in high yields (up to 88%) and with a high degree of purity (99% HPLC) in a time saving and reliable procedure, starting from the 3,5-diiodo derivative of formula I and substantially without isolating any intermediate compound.

Of note, as compound II is optically active, the process of the present invention allow for its preparation by starting from the corresponding optical active isomer, by fully retaining the configuration at the stereocentre during the course of the reaction. Any optical isomers of compound II (i.e. the (S) and the (R) form, as well as any racemic mixture thereof) are to be intended as included in the scope of the present invention.

Figure 3:
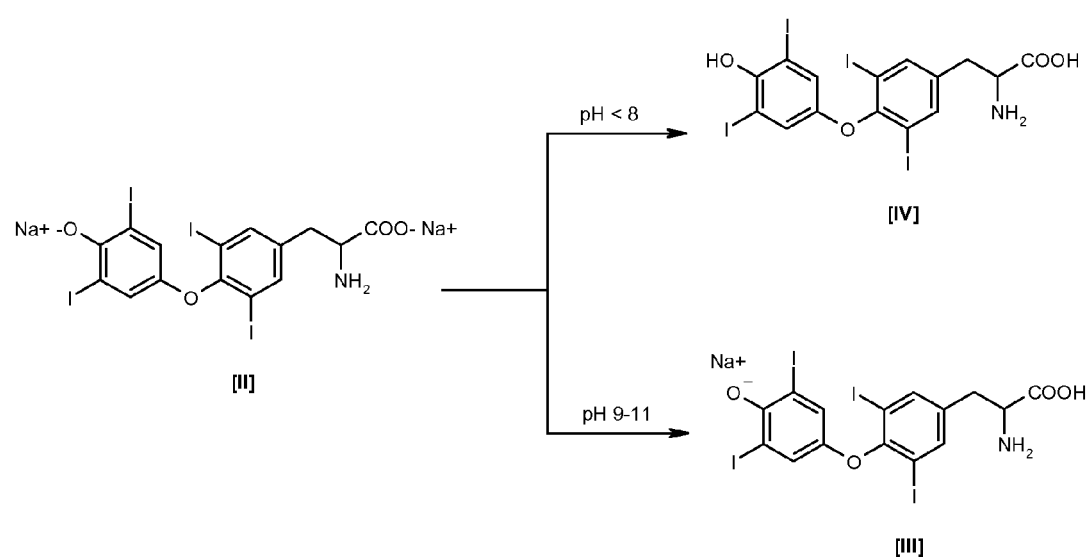

As formerly mentioned, the disodium derivative of formula II may be suitably stored as such or, alternatively, it may be used as precursor of either the L-thyroxine mono-sodium salt of formula III, or in the preparation of the L-thyroxine free form of formula IV, by a proper pH regulation of an aqueous solution of II, and consequent precipitation of the product of choice, as illustrated in the Scheme III, which is identified as FIG. 3.

In this direction, the L-thyroxine monosodium salt of formula III, may be obtained from the corresponding disodium derivative II, for instance, according to the method disclosed in IT1302201 (Bracco), which basically consists in adjusting the pH of an acidic solution of II to a value of about 10, by addition of $Na_2CO_3$, (i.e. by increasing the pH), at high temperature. Remarkably, we have now found that when L-thyroxine disodium salt of formula II is obtained according to the present invention, the mono-sodium derivative III is obtained in higher yields and degree of purity (about 90% starting from II, and 80% overall yield from I, HPLC Area %: 99%, see Example 3 in the Experimental part). According to a further preferred embodiment of the invention, we have also found that the mono-sodium derivative III may be obtained in even higher yields by performing the pH regulation step by adding an acid, such as an organic weak acid, to an alkaline aqueous solution of compound II (i.e. by decreasing the pH), at a high temperature.

Therefore, it is a further aspect of the present invention a process for the preparation of L-thyroxine mono-sodium derivative of formula III comprising the addition of an acid to an alkaline aqueous solution of the corresponding disodium salt of formula II, at a temperature of at least 70° C., to a pH comprised from 9 to 11, followed by cooling at a temperature comprised from about 0° C. to about 25° C. Preferably, the acid is added to a solution at a temperature comprised from about 70° C. to 95° C., more preferably from about 75° C. to 88° C. and even more preferably, from about 82° C. to about 85° C. Preferably the disodium salt of formula II is obtained as formerly reported, and according to another preferred embodiment, the pH is adjusted to a value of about 10.

The pH is monitored, for example, by means of a pH electrode equipment or by any other conventional method.

With the term "alkaline aqueous solution of compound II" we mean a solution containing said disodium derivative in an alkaline base aqueous solution. Preferred alkaline bases comprise alkaline hydroxide or carbonate bases selected from $Na_2CO_3$ and NaOH, whereas the aqueous medium is preferably water or even more preferably distilled water.

As introduced above, the alkaline aqueous solution of II is heated, and the acid of choice is added, preferably dropwise. A representative example of a proper acid may be an inorganic or organic acid, preferably a weak organic acid, even more preferably acetic acid.

After the addition of the acid, the resulting solution is cooled at a temperature preferably comprised from about 10° C. to about 20° C., for example by using a water/ice bath, over a frame of time of about 2 to 5 hours, thus obtaining the L-thyroxine mono-sodium salt III as precipitate. This latter is suitably collected, preferably by filtration, in a proper and characteristic solid form, in very high yield (up to 95% from II and more than 85% from I) and with a high degree of purity (99% HPLC), as indicated in the experimental part herein below.

Before its collection, the filter cake is optionally washed with water, or with an hydro-alcoholic solution, preferably aqueous ethanol, to facilitate recovering of the solid.

The water content of the alkaline solution throughout the precipitation process is chosen for example from the minimum content required for the solubilisation of the reagents, to even higher amounts. Preferably, such a water content is selected from about 11 to about 25 w/w, (whereas w/w means amount of total water with respect to the amount of compound B) being a water content from 11 to 15 w/w particularly preferred, without altering the overall yield, as reported in Table 1 in the Experimental part and in order to modulate precipitation during time (i.e. amount, extent or other features).

Therefore, and according to a particular preferred embodiment of the invention, the mono-sodium derivative of formula III is obtained as a precipitate by addition of acetic acid to an alkaline solution of compound II, being the latter obtained according to the present invention, so to obtain a pH of about 10, at a temperature from about 82° C. to about 85° C. and with a water content of the reaction mixture between about 11 to about 15 w/w, followed by cooling the reaction medium at a temperature from about 10° C. to about 15° C.

As previously mentioned, the present process may be conveniently employed also in the preparation of the L-thyroxine free form of formula IV, by adjusting the pH of an aqueous solution of compound II to values lower than 8, preferably lower than 6.

Preferably, and by analogy to what previously described, the pH regulating agent is an organic or inorganic acid, preferably acetic acid.

The starting materials and any additional reactants of the present process are known in the art and they are commercially available or they also may be prepared in accordance with conventional methods.

From all the above, it can be concluded that the process of the invention enables the preparation of L-thyroxine disodium salt of formula II by reacting the 3,5-diiodo thyronine of formula I with an iodinating agent comprising NaI and $I_2$, advantageously without isolating any intermediate. The method described in the present invention provides an increasing in the yields and in the final degree of purity of the thus obtained derivative, as well as a reduction in the time process, when compared to a similar method known in the prior art, comprising the use of the KI/I$_2$ system as iodinating agent.

As extensively reported, the thus obtained L-thyroxine disodium salt of formula II is efficiently employed in the synthesis of the corresponding L-thyroxine mono-sodium salt III, either according to the prior art teaching or, alternatively and more advantageously, according to the formerly reported procedure, comprising the addition at high temperature of an organic or inorganic acid to an alkaline solution of II at a selected pH, followed by cooling.

In this respect, the present process also enables the preparation of the L-thyroxine free form IV in a very convenient and reliable procedure, by a proper pH regulation of a solution of compound II.

The following examples are herein intended to better illustrate the process of the present invention, without posing any limitation to it.

EXPERIMENTAL PART

Example 1

Preparation of L-Thyroxine Disodium Salt (Compound II) by Reaction of the 3,5 diiodo Thyronine of Formula I with the NaI/I$_2$ System 3,5-diiodo thyronine of formula I (1.0 kg, from Sigma, cat Nr D0629) and NaI (0.3 kg) were suspended in water (8.5 kg), under nitrogen atmosphere, and 70% aq ethylamine (5.6 kg) was added in about 1 h keeping the temperature at about 22° C., obtaining a solution.

A solution of I$_2$ (1.1 kg) and NaI (1.3 kg) in water (5.0 kg) was added over about 3 h maintaining the temperature below 22° C. (product precipitates). The suspension was stirred for about 1 h and then a solution of Na$_2$SO$_3$ (0.1 kg) and Na$_2$CO$_3$ (0.5 kg) in water (2.8 kg) was added. After stirring for about 15 min, the mixture was heated to 50-65° C., to facilitate the solubilisation of the reagents in the reaction medium, and the ethylamine was distilled off under reduced pressure. The remaining reaction mixture was cooled to about 20° C. and acetic acid (0.3 kg) was added until pH of about 11. The suspension was then cooled to 10° C., filtered and the solid washed with water (4.8 kg), obtaining a crude of the compound of formula II.

The wet solid was suspended in water (0.8 kg)/abs ethanol (5.3 kg) mixture and 30% NaOH (0.3 kg), was added (pH>11) The solution was heated to 50-70° C., and then it was cooled to about 10° C. by a water/ice bath, leading to the precipitation of the L-thyroxine disodium derivative of formula II in pure form, which was filtered and washed with cold abs ethanol (yield 86-88%, HPLC 99%).

Example 2

Preparation of L-Thyroxine Mono Sodium Salt (Compound III) Starting from the Disodium Derivative II by Basification/Acidification Step, Wherein II is Prepared According to Example 1

The L-thyroxine disodium derivative of formula II, obtained according to example 1, was dissolved in an aqueous solution of NaOH, according to Table 1 at a temperature of about 25-30° C. After addition of Na$_2$SO$_3$ (0.03 kg) and activated charcoal (3 g), the mixture was stirred for about 0.25-0.30 h and filtered on Millipore (0.45 μm).

The solution was warmed up to about 40-50° C., and aqueous Na$_2$CO$_3$ (see Table 1 below) was added, to constitute an alkaline solution of the monosodium derivative of formula III.

The alkaline solution was heated to a temperature T1 according to Table 1, and acetic acid was added, until a pH of about 9-10. The solution was cooled to about 15° C. over 3 hours and then gently stirred for about 0.5 h. The solid thus precipitated was filtered off, and the filter cake was washed with water (3.0 Kg) and EtOH aq. The thus obtained L-thyroxine mono-sodium salt of formula III (HPLC 99%) was dried at approximately 35° C. under vacuum, giving the desired dried powder.

TABLE 1 operative conditions of Example 2.

| Entry | H$_2$O (w/w)$^a$ | NaOH (eq. mol.)$^b$ | Na$_2$CO$_3$ (eq. mol.)$^b$ | CH$_3$COOH (eq. mol.)$^b$ | T1 (° C.) | Yield (%) |
|---|---|---|---|---|---|---|
| 1. | 11 | 0.50 | 7.43 | 2.42 | 80 | 88 |
| 2. | 11 | 0.42 | 6.32 | 2.06 | 82-85 | 83 |
| 3. | 13 | 0.50 | 7.43 | 2.90 | 80 | 90 |
| 4. | 13 | 0.49 | 7.43 | 2.42 | 82-85 | 88 |
| 5. | 13.5 | 0.44 | 6.69 | 2.18 | 82-85 | 86 |
| 6. | 15 | 0.50 | 7.43 | 2.42 | 70-75 | 84 |
| 7. | 15 | 0.49 | 7.43 | 2.42 | 75-80 | 82 |
| 8. | 15 | 0.49 | 7.43 | 2.42 | 82-85 | 89 |
| 9. | 15 | 0.50 | 7.43 | 2.42 | 85-90 | 81 |
| 10. | 15 | 0.49 | 7.43 | 2.42 | 90 | 83 |
| 11. | 15 | 0.50 | 7.43 | 2.42 | 90-95 | 85 |
| 12. | 16.5 | 0.54 | 8.18 | 2.66 | 82-85 | 83 |
| 13. | 17.5 | 0.49 | 7.43 | 2.42 | 85 | 84 |
| 14. | 17.5 | 0.50 | 7.43 | 2.42 | 90 | 86 |
| 15. | 19 | 0.49 | 14.87 | 3.35 | 90-95 | 85 |
| 16. | 20 | 0.49 | 7.43 | 2.42 | 70-75 | 76 |
| 17. | 20 | 0.50 | 7.43 | 2.42 | 75-80 | 81 |
| 18. | 20 | 0.49 | 7.43 | 2.42 | 82-85 | 84 |
| 19. | 20 | 0.50 | 7.43 | 2.42 | 85-90 | 83 |
| 20. | 20 | 0.50 | 7.43 | 2.42 | 90 | 89 |
| 21. | 25 | 0.49 | 7.43 | 2.42 | 82-85 | 79 |

$^a$amount of total water/amount of compound II
$^b$mol of reactant/mol of compound II Example 3

Preparation of L-Thyroxine Mono Sodium Salt (Compound III) Starting from the Disodium Derivative II, by Acidification/Basification Step, Wherein II is Prepared According to Example 1

Dry L-thyroxine disodium salt of formula II obtained according to Example 1 (1.0 kg) was suspended in water (14 kg) and it was dissolved by adding 30% NaOH (100 g) until a pH of about 12-13 (if necessary the mixture was heated to 25-30° C.).

After addition of Na$_2$SO$_3$ (20 g) and activated charcoal (3 g), the mixture was stirred for about 0.5 h and filtered on Millipore (0.45 μm). The filter is washed with water (1 kg) and HCl is added until pH 2-3, thus obtaining a precipitate.

The suspension was heated and a solution of Na$_2$CO$_3$ (2.0 kg) in water (6 kg) was added maintaining the temperature at about 90-95° C., obtaining by that a clear solution.

The solution was cooled at about 20° C. causing the formation of a precipitate. The suspension was filtered and the cake was washed with water (1.5 kg).

Wet L-thyroxine mono-sodium of formula III was dried with a yield of 92.0% from II, corresponding to an overall yield from 1 of 80% (HPLC Area %: 99.

BRIEF DESCRIPTION OF THE SEVERAL VIEWS OF THE DRAWING(S)

Figure 1:
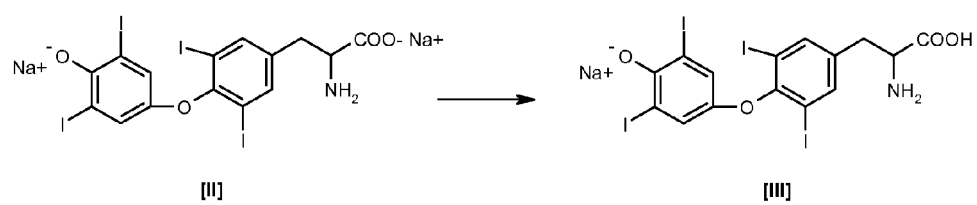

FIG. 1: Preparation of the monosodium salt of L-thyroxine (compound of Formula III) by controlled acidification of the corresponding disodium salt (compound of Formula II).

FIG. 2: Preparation of the disodium salt of L-thyroxine (compound of Formula II) i.e. according to IT1302201 by iodination of compound of Formula I with $KI/I_2$ in the presence of a suitable amine. The mono and di-potassium salts mixture is subjected to a subsequent separation and purification steps, including:(a) the addition of an organic acid; (b) the separation of the thus obtained "free form" (as a precipitate); and (c) the addition of an excess of sodium hydroxide to obtain the L-thyroxine di-sodium salt of Formula II.

FIG. 3: The disodium derivative of L-thyroxine (Formula II compound) may be the precursor of either the L-thyroxine mono-sodium salt of Formula III, or of the L-thyroxine free form of Formula IV, by a fine pH regulation of an aqueous solution of Formula II compound and precipitation of the product of choice, according to Scheme III.

The invention claimed is:

1. A process for the preparation of a thyroid hormone derivative of formula II:

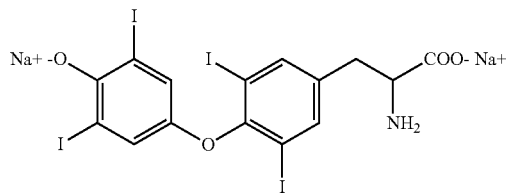

comprising the following steps:
a) reacting a compound of formula I:

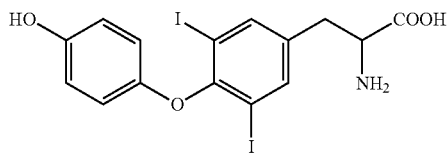

with an iodinating agent comprising NaI and $I_2$, in the presence of an aliphatic amine to obtain the disodium derivative of formula II recovered as a crude;
  b) preparing a hydroalcoholic alkaline solution of the crude compound of formula II, having a pH of at least 11;
  c) heating at a temperature of 40° C. to 80° C.;
  d) cooling to a temperature of 5° C. to 20° C.; and
  e) isolating compound II as a pure solid.

2. The process according to claim 1, wherein the aliphatic amine is a linear mono $C_1$-$C_4$ amine.

3. The process of claim 2, wherein said aliphatic amine is ethylamine.

4. The process according to claim 1, wherein the molar ratio between NaI and $I_2$ in the iodinating agent is from 1 to 4.

5. The process according to claim 4, wherein the molar ratio between NaI and $I_2$ in the iodinating agent is from 2 to 3.

6. The process according to any one of claim 1 or 4, wherein the iodinating agent is added to a solution comprising compound I and the aliphatic amine, at a temperature not higher than 25° C.

7. The process according to claim 1, wherein the iodinating agent is prepared in distilled water.

8. The process according to any one of claim 1 or 4, further comprising re-suspending the compound of formula II in an alkaline aqueous solution, adding an organic or inorganic acid to the aqueous solution, to a pH of 9-11 and isolating the mono-sodium derivative of formula III:

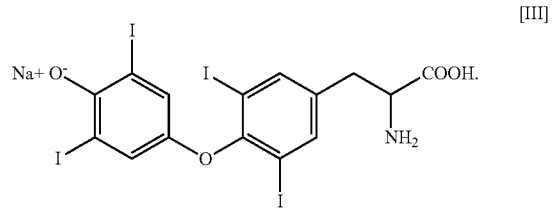

9. The process according to claim 8, wherein the acid is acetic acid.

10. The process according to claim 8, wherein the acid is added to the aqueous solution of II, heated to a temperature of 70° C. to 95° C., and cooling the resulting solution to a temperature of 10° C. to 15° C.

11. The process according to claim 10, wherein the acid is added to the aqueous solution of II at a temperature of 82° C. to 85° C.

12. The process according to claim 8, wherein the water content of the aqueous solution of II is from 11 w/w to 25 w/w.

13. The process according to claim 12, wherein the water content of the aqueous solution of II is from 11 w/w to 15 w/w.

14. The process according to claim 10, wherein the acid is added to the aqueous solution of II at a temperature of 75° C. to 88° C., and said solution has a content of water from 11 to 15 w/w.

15. The process according to claim 14, wherein said acid is acetic acid.

16. The process according to claim 15, wherein said temperature is 82° C. to 85° C.

* * * * *

UNITED STATES PATENT AND TRADEMARK OFFICE
CERTIFICATE OF CORRECTION

PATENT NO. : 8,759,572 B2  
APPLICATION NO. : 13/515712  
DATED : June 24, 2014  
INVENTOR(S) : Viscardi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this  
Fourth Day of August, 2015

Michelle K. Lee  
*Director of the United States Patent and Trademark Office*